United States Patent [19]

Wilson

[11] Patent Number: 5,466,459
[45] Date of Patent: Nov. 14, 1995

[54] WAX AND CAPSAICIN BASED PESTICIDE

[75] Inventor: Walter R. Wilson, Pulaski, Pa.

[73] Assignee: Wilder Agricultural Products Co., Inc., Pulaski, Pa.

[21] Appl. No.: 147,463

[22] Filed: Nov. 3, 1993

Related U.S. Application Data

[63] Continuation of Ser. No. 903,501, Jun. 24, 1992, abandoned.

[51] Int. Cl.$^6$ ............................ A01N 25/32; A01N 65/00
[52] U.S. Cl. ..................... 424/407; 424/195.1; 424/409; 424/400; 424/405; 514/919
[58] Field of Search ..................... 424/405, 409, 424/485, 502, 195.1, 196.1, 406, 407, 400; 574/919, 787, 920

[56] References Cited

U.S. PATENT DOCUMENTS

| | | | |
|---|---|---|---|
| 2,159,953 | 5/1939 | Proetto | 167/24 |
| 4,097,607 | 6/1978 | Larson | 424/324 |
| 4,230,687 | 10/1980 | Sair et al. | 424/22 |
| 4,439,488 | 3/1984 | Trimnell et al. | 428/402.24 |
| 4,557,934 | 12/1985 | Cooper | 424/128 |
| 4,911,952 | 3/1990 | Doane et al. | 427/213.31 |
| 4,961,929 | 10/1990 | Gurvich et al. | 424/196.1 |
| 4,963,591 | 10/1990 | Fourman et al. | 514/944 |
| 5,221,535 | 6/1993 | Domb | 424/450 |
| 5,227,162 | 7/1993 | Ferrari | 424/195.1 |
| 5,240,708 | 8/1993 | Plummer et al. | 424/405 |

*Primary Examiner*—Thurman K. Page
*Assistant Examiner*—Neil Levy
*Attorney, Agent, or Firm*—Oldham & Oldham, Co.

[57] ABSTRACT

This invention relates to a capsaicin-based, refined wax based pesticide which is, environmentally safe pesticide. The pesticide is coupled with a naturally-produced central nervous system stimulant and other naturally-produced irritants, antioxidants; insect repellents, scents, and soil nutrients. Through the synergy between the physical contraction of the wax base, containing capsaicin, as it dehydrates coupled with the higher vapor pressure (volatility) of the scent package, leads to a natural migration of the scent package to the surface of the waxy base thereby maintaining effectiveness for a longer period of time with a decreased frequency of application.

7 Claims, 1 Drawing Sheet

WAX AND CAPSAICIN BASED PESTICIDE

This is a continuation of application Ser. No. 07/903,501 filed on Jun. 24, 1992, now abandoned.

TECHNICAL FIELD

This invention relates to a totally organic pesticide which effects its function by physically changing the environment of the organism, thereby mechanically disrupting its ability to function.

BACKGROUND OF THE INVENTION

There are several ways to protect useful and ornamental plants against pests, disease and weeds. The simplest, yet most ineffective way is purely mechanical removal of weeds and pests. The most common method is the use of chemical control agents, because of their ease of application. However, the use of chemical agents often invokes the disadvantage of unwanted side effects which may be attributed, for example, to high toxicity or inadequate degradability, and in the case of pests, the development of resistance, often after only a short period of time.

In particular, pests such as the spider mite are particularly troublesome. Spider mites belong to the family of Acari known scientifically as Tetranychidae, and are a common form of agricultural pest which damage the foliage of plants. Two common species of spider mites are the carmine (red) spider mite (*Tetranychus cinnabarinus*) and the two-spotted spider mite (*Tetranychus urticae*), both of which can inflict damage and reduce yields of growing crops and plants.

Various miticides are presently available to combat infestations of spider mites by killing such pests. One popular miticide is dicofol, commercially available from Rohm & Haas Company of Philadelphia, Pa. under the tradename "KELTHANE".

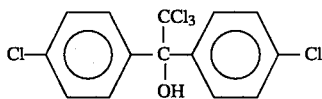

Another popular miticide is a micronized form of sulfur, commercially available from Cumberland International of Houston, Tex., under the tradename "SULFLOX". A third type of popular miticide is 2-(p-tert-butylphenoxy) cyclohexyl-2-propynyl sulfite, commercially available from Uniroyal Chemical, a division of Uniroyal, Inc. under the tradename "COMITE".

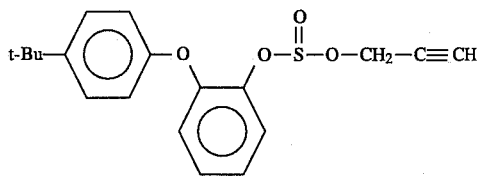

Still another commercially available miticide is sold under the tradename AVID, a spiro[11,15-methano-2H, 13H, 17H-furo[4,3,2-pq][2,6]benzodioxacyclooctadecin-13,2'-[2H]pyran], avermectin B1 derivative, available from Merck & Co., Inc. of Rahway, N.J. Yet another miticide is sold under the tradename TALSTAR, a cyclopropanecarboxylic acid, 3-(2-chloro-3,3,3-trifluoro-1-propenyl)-2,2-dimethyl-, (2-methyl[1,1'-biphenyl]-3-yl)methyl ester, [1.alpha.,3.alpha.(Z)]-(.±.)-, available from FMC, Philadelphia, Pa.

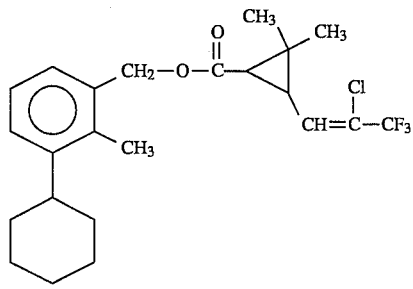

Yet another product is bi-2,4-cyclopentadien-1-yl,1,1',2,2',3,3',4,4',5,5'-decachloro- or bis(pentachloro-2,4-cyclopentadien-1-yl), sold under the tradename PENTAC AQUAFLOW, available from Sandoz, Ltd., Basel Switzerland.

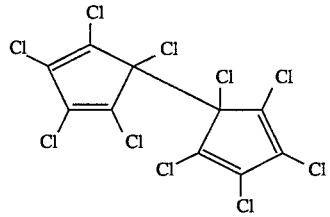

And still another product is sold under the tradename SAFER soap, commercially available from Safer Inc., Newton, Mass.

While such miticides are generally effective against spider mites in the short term, spider mites reproduce rapidly, and resistant strains develop an increased tolerance of such miticides over a period of time. It is also believed that spider mites must actually come in physical contact with such miticides in order to be killed thereby. However, as compared with other agricultural pests, spider mites move relatively little, and are therefore less likely to come into physical contact with applied miticides unless relatively large amounts of such miticides are applied.

However, with all of the typical pest control methods currently in use, there is no product currently available which is environmentally safe, to which insects do not quickly develop a resistance to.

SUMMARY OF THE INVENTION

In accordance with the present invention, there is provided a longer-lasting, environmentally safe, pesticide which effects a physical change in the organisms' ecosystem thereby mechanically disrupting its ability to function, coupled with a naturally-produced central nervous system stimulant and other naturally-produced irritants, antioxidants, insect repellents, scents, and soil nutrients.

It is an object of this invention to provide a totally natural pesticide.

It is a second object of this invention to provide a pesticide which provides effective protection against insects for an extended period of time.

It is a third object of this invention to provide a pesticide which uses only naturally-occurring additives to enhance the pesticidal characteristics of the product.

It is a fourth object of this invention to provide a pesticide which will be effective as a pesticide without producing resistant strains of insects after repeated usage of the pesticide.

It is a fifth object of this invention to provide a pesticide wherein the mode of killing the insects is via a mechanical suffocation process.

It is a sixth object of this invention to provide a pesticide crop protector which is also an anti-transpirant.

It is a seventh object of this invention to provide a pesticide which is also a fertilizer.

It is an eighth object of this invention to provide a pesticide which is effective against a wide variety of insects which cause crop loss of vegetables, fruits, roses and flowers, grasses, turf, trees and shrubs.

These and other objects of this invention will be evident when viewed in light of the detailed description and appended claims.

BRIEF DESCRIPTION OF THE DRAWINGS

The invention may take physical form in certain parts and arrangements of parts, a preferred embodiment of which will be described in detail in the specification and illustrated in the accompanying drawings which form a part hereof, and wherein.

DETAILED DESCRIPTION OF THE INVENTION

Figure 1:
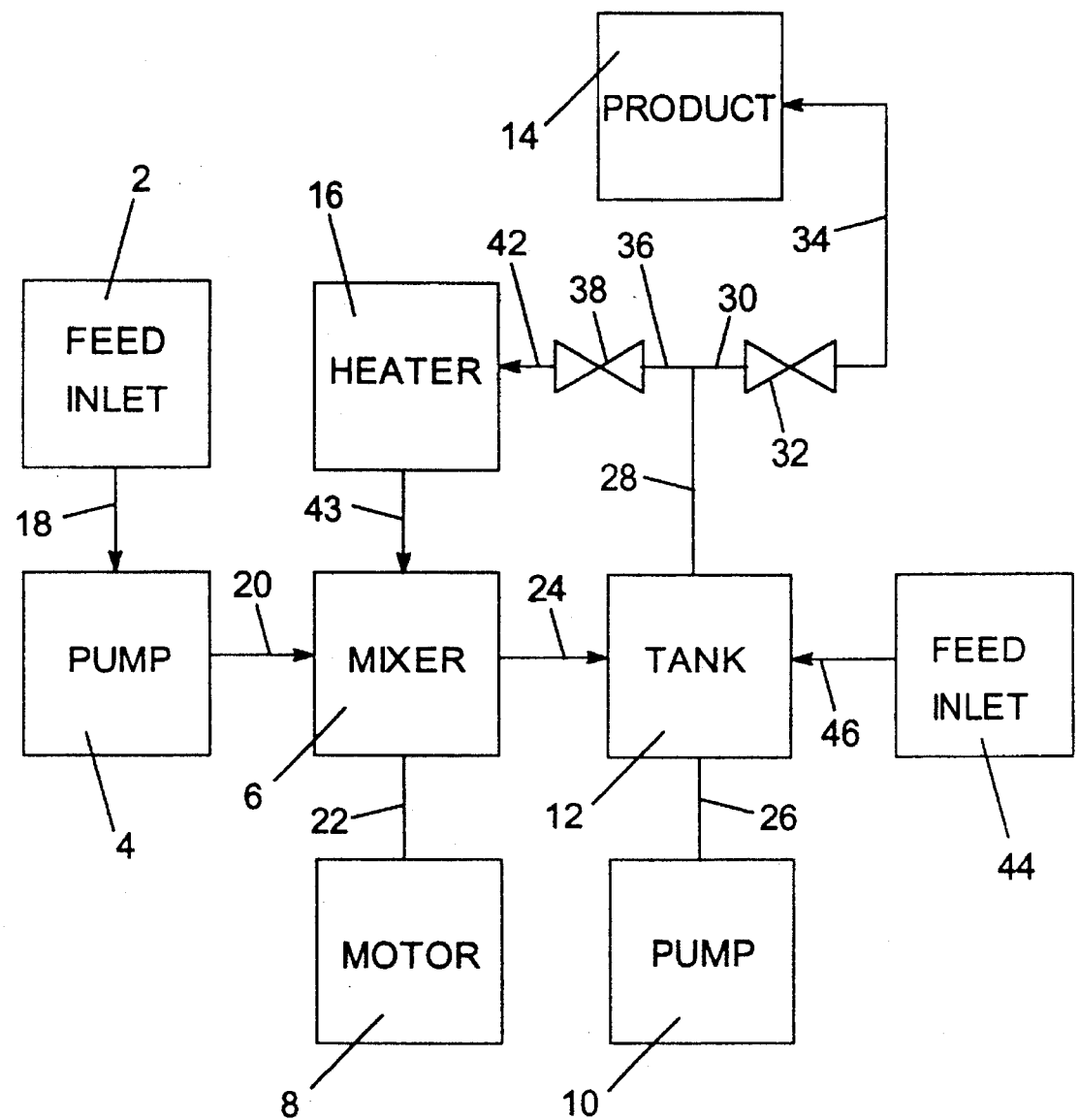
FIG. 1 is a flow diagram of the process used in the preparation of the pesticide.

The organic pesticide, tradenamed, Hot Pepper Wax™, of this invention is a multicomponent mixture of ingredients, each with a specified purpose. In general, the product uses a refined wax base. Refined wax is made by the elongation of long chain hydrocarbon wax molecules with water. Refined wax is inert, and Federal Drug Administration (FDA) approved for use on all edibles.

While the exact nature of the initial wax is not critical, in general, it will be a low-melting compound of high molecular weight, solid at room temperature. Common properties which must be exhibited by the wax is water repellency, smooth texture, nontoxicity, and freedom from objectionable odor and color. Specifically, the wax can be described as an aliphatic hydrocarbon, characterized by a straight or branched carbon chain. In generic formula, it is characterized as $C_2H_{2n+2}$.

As the refined wax dries, the water component evaporates causing the long chain molecules to shorten. Refined wax is white when applied, but as it dries, becomes clear. Although wax and water do not mix, they can be held together, thereby leading to the white appearance. A waxy coating however, by itself, is only partially effective in killing insects, particularly mites. While not wishing to be bound by theory, the natural property of refining wax to contract upon moisture content evaporation, is speculated to effect a mechanical killing of the mites through suffocation.

One additional benefit of employing a waxy base to the plant foliage is the anti-transpirant properties associated with the application. Natural evaporation is slowed through the waxy layer thereby promoting water conservation in more arid climates.

Supplementing this naturally protective waxy coating is the incorporation of capsaicin extract of Cayenne pepper. The extract has at least two intriguing qualities. First it is harmless to plants, and-secondly, it is the active principal that makes Cayenne pepper hot. Capsaicin is a powerful central nervous system (CNS) stimulant. It is unique in that it produces heat and is measured in Heat Units (HU). In producing Capsaicin extract, the interest is primarily in the percent of Capsaicin to extraneous matter. This percent can be dramatically increased by polyploidy of *Capsicum frutescens*. Polyploidy is the condition of multiple sets of chromosomes, it creates sports or plants of increased yield or potency. It is an arduous process in that it requires interfering with the separation of mother/daughter cells at the time mitosis or cell-splitting occurs.

By applying capsaicin extract and refined wax in an aqueous suspension, an effective miticide can be produced and applied to plants. However, the lasting effect of the capsaicin extract and refined wax is quite limited, and requires a daily application to insure effectiveness.

However, through the addition of additional scents to the pesticide formulation, an increase in effectiveness can be achieved with a decrease in application rate. This scent module is created from plant extracts of plants that naturally repel insects. A tincture (alcohol extract) was prepared of mustard (an irritant of *Brassica nigra*), rosemary (an antioxidant with similar preservative properties to BHA (butylated hydroxyanisole) and BHT (butylated hydroxytoluene), and bioflavonoids (natural insect repellents) from orange and lemon. Additionally, it has been found effective to add tinctures of garlic, onion, parsley, basil, thyme, coriander, and cumin to the scent package. Each of these extracts are taken from the raw fruit or herb, and in some cases, are milled into the wax. This scent package is added to the refined waxy base in a titrated form as only minute doses are needed. The ability of an insect to detect smells is far greater than that of other organisms.

Since the pesticide is not absorbed into the plant or fruit, it does not impart a flavor to treated fruit. The higher rotating form of the capsaicin migrates to the surface of the wax as a fine oil. This happens as a result of the shortening of the long chain molecules of the wax as a direct result of the dehydration process, i.e, a divisional separation or zoning occurs, much like chromatography. The pesticide may be easily removed from the fruit with warm water, as the wax softens and carries the constituents away with the water. Dispersement of the oils will occur naturally, within two weeks as the oils are volatile. Dispersement is logarithmic, with a mean half life of seven days. Following seven days, the oils disperse much quicker, with 80% of the oils gone in ten days.

The synergy between the naturally contracting waxy base containing capsaicin coupled with the higher vapor pressure (volatility) of the scents, leads to a natural migration of the of the scent package to the surface of the waxy base. Waxy-based pesticide material with capsaicin required a daily application to retain its pesticidal qualities. With the incorporation of the scent package, effectiveness was maintained for a longer period of time with a decreased frequency of application. The surface migration of the additive scents is speculated to effect this desirable result.

Plants that have been attacked by insects are susceptible to various fungi, bacteria and viral infections. This infection could be carried on the bugs, or is a result of the insects. In fact, in some cases, it is the fungus, or mosaic, that kills the plant, not the insects. Commercial preparations sometimes contain chemical fungicides and bacticides in prophylactic doses to prevent, not necessarily stop infection. Wetting any diseased plant invites infection and while incorporation of these types of supplements are considered safe by law, they are not desirable in a totally natural pesticide.

Eucalypts are particularly disease free. In fact, eucalyptus oil has been used for hundred of years as an active germicide, possessing antiseptic and astringent qualities. It is probably best known for its use in vaporizers to help relieve respiratory ailments. Eucalyptus is classified by the FDA as non-toxic. Therefore, the incorporation of extract of eucalyptus globulus into the pesticide imparted anti-bacterial, anti-fungicidal efficacy to the pesticide in a natural way.

Optionally, since the pesticide contains an aqueous environment, in a preferred embodiment, the pesticide will include a water soluble nutrient package. such nutrient package will typically include kelp (seaweed) with appropriate amounts of vitamins and minerals which act as a fertilizer. In a most preferred embodiment, this fertilizer package will be time-released into the soil by the application of additional moisture to the plant foliage coated with the pesticide/nutrient package. The naturally solubility of the nitrogen, phosphorus, and potassium components in the nutrient package will supplement the soil composition as droplets of moisture collect on the leaves and subsequently drop to the ground.

EXAMPLES

In general, the pesticide can be characterized as described in Table I.

TABLE I

| | | |
|---|---|---|
| Active Ingredients | Nitrogen (N) | 1% |
| | Phosphoric Acid ($P_2O_5$) | 0% |
| | Potash ($K_2O$) | 1% |
| | Paraffin Wax | 40% |
| Inert Ingredients | Extract of Hot Pepper | 10% |
| | Extract of Scent Pkg.[1] | 1% |
| | Extract of Eucalyptus | 1% |
| | Water | 46% |

[1]Scent package includes tincture of garlic, onion, parsley, basil, thyme, coriander, cumin, mustard, rosemary, orange and lemon.

Alternatively, the pesticide can be formulated as:

TABLE II

| | | |
|---|---|---|
| Active Ingredients | Capsicum extract[a] | 33% |
| | Scent extract[b] | 2% |
| Inactive Ingredients | Water | 54% |
| | Paraffin wax | 9% |
| | Mineral Oil | 2% |

[a]Capsicum extract contains
(1) select capsicums of *C. annuum* & *C. frutescens*
[b]Scent extract contains
(1) extractives and tinctures of select fruits, flowers, leaves & roots of mustard, rosemary, orange, lemon, garlic, onion, parsley, basil, thyme, coriander & cumin
(2) eucalyptus oil U.S.P.
(3) kelp The extractives contain distilled grain vinegar and sodium chloride, while the tinctures contained distilled grain alcohol.

Preparation

The key to the preparation of the pesticide is the ability to reduce the particle size of the waxy base until the basic wax structure is microcrystalline. To a spinning vortex of water, the microcrystalline wax is combined to produce a milky white liquid. Critical to the preparation is the centrifugal velocity of the suspended particles in the liquid. After sufficient mixing has occurred, capsaicin is added to the suspended mixture followed by the addition of appropriate additives. The speed of the rotating suspension insures a good mechanical attachment of the ingredients to the waxy base.

Capsicum Extract

During the preparation of capsicum extract, select capsicums of *C. annuum* and *C. frutescens* are dried, ground, dehydrated, and milled into a fine powder. This powder is combined with distilled grain vinegar and sodium chloride (NaCl) and blended at high speed for several minutes. The resulting vegetative matter and solution are cooked for at least 24 hours at low temperature in a ceramic crock. The cooked solution is blended at high speed and diluted with distilled grain vinegar to a uniform strength. The solution of uniform strength is then passed through a sieve under pressure to produce an end product free of extraneous vegetative matter.

Scent Extract

In preparing the scent extract, select fruits, flowers, leaves and roots of mustard, rosemary, orange, lemon, garlic, onion, parsley, basil, thyme, coriander and cumin are dried, ground, dehydrated, and milled into a fine powder. This powder is combined with kelp meal, distilled grain vinegar and sodium chloride (NaCl). This mixture is blended at high speed for several minutes. The resulting vegetative matter and solution are cooked for at least 24 hours at low temperature in a ceramic crock. The cooked solution is blended at high speed. The resulting solution is separated from the vegetative matter by fine filtering. This solution is subsequently concentrated by evaporation to a uniform strength.

The vegetative matter from the water stage of the scent extract is dried, saturated with distilled grain alcohol, and expressed several times to yield a light yellow oil. This oil is filtered and diluted with distilled grain alcohol to produce a scent oil of uniform strength. The scent oil is combined with Eucalyptus oil U.S.P. and passed through a column of activated charcoal. The resulting combination oil is the oil phase of the scent extract.

Reactor

With reference to FIG. 1, sufficient water is added into feed inlet 44 such that upon entry into tank 12 through tank inlet tube 46, there will be an adequate amount of water in tank 12 such that when rotary pump 10 which is in communication with tank 12 through connecting means 26, proper circulation will be effected throughout the system. Water under force is sent through tank outlet 28, which pathway bifurcates into recirculating pathway 36 or product outlet 30. A pair of ball valves 32, 38 control the direction of the path. During product preparation, ball valve 32 is in a closed position, while ball valve 38 is in an open position thereby permitting flow through heater inlet 42 into heater 16, which initially, is not turned on. The water continues through heater outlet 43 into the mixing cavity 6 and converted into a vortex that produces a venturi when the high speed motor 8 which is in communication with mixer 6 via connector 22 is turned on. The path is completed by the venturi created by mixer 6 moving through mixer outlet 24 into tank 12.

Capsicum extract is added via feed inlet 44 through tank inlet tube 46 into tank 12 in the proper proportion. After sufficient mixing, the water phase of the scent extract is added in a similar manner. After sufficient mixing, the microcrystalline findings of the refined Paraffin wax U.S.P. are added to tank 12 also in a manner similar to the previous extracts. The temperature is raised in the mixer 6 by heater 16 until the findings adhere themselves to the capsicum-scent liquid.

The oil phase of the scent extract is combined with mineral oil in feed inlet 2 to form an emulsifier that is injected under high pressure from feed inlet 2 through pump inlet 18 and high pressure pump 4 into the stream of the vortex and into the venturi by mixer inlet 20

TABLE IV-continued

Product Effectiveness and Phytotoxicity

| Pesticide | Effectiveness[a] | Initial kill (3 days)[b] | Phytotoxicity[c] | Applicability[d] |
|---|---|---|---|---|

[b]Initial kill of mite population measured at 3 days after initial application
[c]Phytotoxicity to subject plant
none-no effect
mild-minor burning and/or wilting
moderate-major burning and/or wilting, leaf drop and/or distortions
severe-plant loss or death
[d]approved for use on ornamental plants and/or food crops
[e]pending approval with FDA As is clearly seen in Table IV, the organic pesticide of the invention, HOT PEPPER WAX™ is an effective eradicant against the two-spotted spider mite with no phytotoxicity to the host plant. While there are other products which are more effective in this process, none of these products are totally organic and derived from plant sources. The unanticipated synergistic interaction between the scent extract, the capsicum extract, coupled together in the paraffin wax, provides an environmentally safe pesticide to which insects do not develop an increased tolerance to. The synergy between the naturally contracting waxy base, due to slow dehydration, which contains the capsaicin, coupled with the higher vapor pressure (volatility) of the scents, leads to a natural migration of the scent package to the surface, thereby enhancing the effectiveness of the product. The ability to incorporate a water soluble nutrient package into the pesticide, typically kelp (seaweed) with appropriate amounts of vitamins and minerals promotes the usefulness of the product.

What is claimed is:

1. A topically applied non-penetrating pesticide containing only natural ingredients with no phytotoxicity to a host plant consisting essentially of:
   (a) an aliphatic hydrocarbon microcrystalline waxy base, from 9 to 40% by total weight, impregnated with a sufficient quantity of water such that as the water evaporates, the base will contract;
   (b) an irritant, from 10 to 33% by total weight, which is a hot pepper extract selected from the group consisting of capsaicins, C.frutescens and C. annuum dispersed throughout the waxy base; and
   (c) at least one scent, from 1 to 2% by total weight, selected form the group consisting of a tincture of garlic, onion, parsley, basil, thyme, coriander, cumin, mustard, rosemary, orange and lemon, the scent having
      (1) an alcohol soluble oil phase, and
      (2) a water soluble component,
   wherein an interaction of an alcoholic part of the tincture facilitates the migration of the scent to an exterior surface of the wax, the scent which has a lower vapor pressure than the alcohol, being transported through the waxy matrix through its solubilization in alcohol, which has a higher vapor pressure, thereby permitting additional scent to reach the exterior surface than would otherwise be possible if the scent was used alone, the waxy base, irritant, and scent combination being capable of being washed from the plant or fruit without any deleterious effect on the plant in that the treatment is non-invasive and non-penetrating, the pesticide having been prepared by the steps of:
   (i) suspending the microcrystalline waxy base in a spinning vortex that produces a venturi of water using a centrifugal velocity mixing technique;
   (ii) adding the irritant to the waxy base, the irritant having been previously extracted with at least one extracting agent, heated for at least 24 hours, and strained to produce the irritant essentially free of extraneous vegetative matter;
   (iii) adding the water-soluble scent to the waxy base, the scent having been previously extracted with at least one extracting agent, heated for at least 24 hours, and strained to produce the water soluble component of the scent essentially free of extraneous vegetative matter;
   (iv) adding the alcohol soluble oil phase of the scent, the extraneous vegetative matter of the previous step having previously been diluted with alcohol to make the alcohol soluble oil component, the addition of the irritant and the scent extract occurring in a centrifugal mixer to produce a rotating suspension of the pesticide, a speed of the rotating suspension insuring a good mechanical attachment of the irritant and the scent to the waxy base; and
   (v) straining the pesticide under pressure.

2. The pesticide of claim 1 which further includes a soluble fertilizer.

3. The pesticide of claim 2 wherein the soluble fertilizer is kelp, vitamins and minerals.

4. The pesticide of claim 3 which further includes a germicide.

5. The pesticide of claim 4 wherein the germicide is an extract of eucalyptus.

6. The pesticide of claim 1 wherein the pesticide is an aqueous suspension.

7. The pesticide of claim 6 wherein the aqueous suspension is 10 solids weight percent.

* * * * *